(12) United States Patent
Hurson et al.

(10) Patent No.: US 6,527,554 B2
(45) Date of Patent: Mar. 4, 2003

(54) NATURAL IMPLANT SYSTEM (75) Inventors: Steven M. Hurson, Yorba Linda, CA (US); Mickey Ray Dragoo, Escondido, CA (US)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/873,794

(22) Filed: Jun. 4, 2001

(65) Prior Publication Data

US 2002/0182567 A1 Dec. 5, 2002

(51) Int. Cl.⁷ .................................................. A61C 8/00
(52) U.S. Cl. ........................................ 433/173; 433/174
(58) Field of Search .............................. 433/172, 173, 433/174

(56) References Cited

U.S. PATENT DOCUMENTS

| | | | | |
|---|---|---|---|---|
| 4,812,120 A | * | 3/1989 | Flanagan et al. | ............ 433/173 |
| 4,826,434 A | * | 5/1989 | Krueger | ...................... 433/174 |
| 5,310,343 A | | 5/1994 | Hasegawa et al. | |
| 5,344,457 A | * | 9/1994 | Pilliar et al. | ................. 433/174 |
| 5,417,568 A | | 5/1995 | Giglio | |
| 5,584,693 A | * | 12/1996 | Nishihara | .................... 433/169 |
| 5,588,838 A | * | 12/1996 | Hansson et al. | ............ 433/173 |
| 5,639,237 A | * | 6/1997 | Fontenot | .................... 433/173 |
| 5,674,069 A | | 10/1997 | Osorio | |
| 5,759,034 A | | 6/1998 | Daftary | |
| 5,779,480 A | | 7/1998 | Groll et al. | |
| 5,779,481 A | * | 7/1998 | Aires | .......................... 433/173 |
| 5,816,813 A | * | 10/1998 | Hansson et al. | ............. 433/174 |
| 5,989,027 A | | 11/1999 | Wagner et al. | |
| 6,164,969 A | | 12/2000 | Dinkelacker | |
| 6,174,167 B1 | | 1/2001 | Wohrle | |
| 6,217,331 B1 | * | 4/2001 | Rogers et al. | ............... 433/173 |
| 6,217,333 B1 | | 4/2001 | Ercoli | |
| 6,220,861 B1 | * | 4/2001 | Kwon et al. | ................. 433/173 |
| 6,227,857 B1 | * | 5/2001 | Morgan et al. | ............. 433/173 |
| 6,227,858 B1 | | 5/2001 | Lundgren | |
| 6,231,342 B1 | | 5/2001 | Osorio et al. | |
| H1984 H | | 8/2001 | Salama et al. | |
| 6,283,754 B1 | * | 9/2001 | Wöhrle | ........................ 433/173 |

FOREIGN PATENT DOCUMENTS

DE   42 39 060 A1   11/1992

\* cited by examiner

*Primary Examiner*—Ralph A. Lewis
(74) *Attorney, Agent, or Firm*—Knobbe, Martens, Olson & Bear, LLP (57) ABSTRACT

A dental implant for supporting a dental prosthesis comprises a body portion and an abutment portion. The dental implant including a roughened surface. When the dental implant is installed into a patient's jawbone, the roughened surface extends above a crest of the jawbone. In one arrangement, the roughened surface extends at least 2 millimeters above the crest. In another arrangement, the roughened surface extends at least 3 millimeters above the crest. In yet another arrangement the roughened surface extends at least 4 millimeters above the crest. Methods for installing and manufacturing a dental implant are also disclosed.

23 Claims, 11 Drawing Sheets

NATURAL IMPLANT SYSTEM

BACKGROUND OF THE INVENTION

1. Field of the Invention

The present invention relates generally to dental implants and, more particularly, to an improved implant with a zone for soft tissue attachment.

2. Description of the Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone) of a patient. The oral surgeon first accesses the alveolar bone through the patient's gum tissue and removes any remains of the tooth to be replaced. Next, the specific site in the alveolar bone where the implant will be anchored is widened by drilling and/or reaming to accommodate the width of the dental implant to be implanted. Then, the dental implant is inserted into the hole, typically by screwing, although other techniques are known for introducing the implant in the jawbone.

After the implant is initially installed in the bone, a temporary healing cap is secured over the exposed proximal end in order to seal an internal bore of the implant. The patient's gums are then sutured over the implant to allow the implant site to heal and to allow desired osseointegration to occur. Complete osseointegration typically takes anywhere from four to ten months.

During stage II, the surgeon reaccesses the implant fixture by making an incision through the patient's gum tissues. The healing cap is then removed, exposing the proximal end of the implant. Typically, an impression coping in attached to the implant and a mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or attached to the implant during stage I. In such a procedure, stages I and II are effectively combined in to a single stage.

Stage III involves fabricating and placement of a cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosthesis to the final abutment.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The final abutment typically lies on the top surface and extends through the soft tissue, which lies above the alveolar bone. As mentioned above, the abutment supports the final prostheses. Typically, the coronal or crown portion of the collar and the portions of the final abutment that extend through the soft tissue have a machined or polished surfaces. This arrangement is believed in the art to prevent the accumulation of plaque and calculus and facilitates cleaning.

SUMMARY OF THE INVENTION

One aspect of the present invention includes the recognition that the body's natural defense mechanisms tend to provide approximately a 2–3 millimeter zone of soft tissue between the abutment-implant interface (i.e., microgap) and the alveolar crest. This zone is referred to as the "biological width" and is present around natural teeth as well as dental implants. The biological width typically extends 360 degrees around the implant and lies coronal to the alveolar crest and apical to the prosthetic crown margin (approximately 2.5–3 millimeters). The biological width consists of approximately 1 millimeter gingival sulcus, 1 millimeter epithelial attachment and 1 millimeter connective tissue attachment. In prior art implants, the abutment-implant interface typically lies flush with the alveolar crest. As such, the bone tissue is reabsorbed and the alveolar crest retreats until the proper biological width can be reestablished. This bone loss is undesirable both aesthetically and structurally.

Another aspect of the present invention includes the recognition that the smooth surfaces of the collar and the abutment tend to inhibit the attachment of connective soft tissues. Accordingly, bone tissue is reabsorbed and the soft tissue and alveolar crest typically move a distance down of approximately 1–2 millimeters from the smooth surfaces of the collar and/or abutment. As mentioned above, such bone loss is undesirable.

Yet another aspect of the invention is the recognition that in the prior art typically provides for a flat interface (i.e., microgap) between the abutment and the collar of the implant. However, due to the irregular configuration of the alveolar crest, a flat interface makes it difficult to conform to a proper biological width in all 360 degrees around the implant. A proper biological width that does not extend for all 360 degrees around the implant can produce undesirable bone loss.

One aspect of the present invention provides for a one piece dental implant, which has a roughened surface which extends above the alveolar crest. This roughened surface allows connective tissue to attach to the implant. In one application of the invention, the coronal portion above the alveolar crest of the collar and implant is prepared similar to a natural tooth by providing approximately 360 degrees of at least about a 2 millimeter zone of roughened surface above the alveolar crest. Preferably, the implant is provided with approximately 360 degrees of at least a 3 millimeter zone of roughened surface above the alveolar crest. More preferably, the implant is provided with approximately 360 degrees of at least a 4 millimeter zone of roughed surface above the alveolar crest. In modified arrangements, the dental implant comprises more than once piece while still providing approximately 360 degrees of 2–4 millimeters or more of roughened surface above the alveolar crest.

Still yet another aspect of the invention is a method for installing a dental prosthesis into a patient's mouth. A dental implant is provided. The dental implant include a body portion at a distal end of the dental implant, an abutment portion at a proximal end of the dental implant and a collar portion located between the body portion and the abutment portion. The collar portion includes an outer surface with a tissue attachment portion, which preferably is roughened. The dental implant is installed into the patient's jawbone such that the body portion lies substantially beneath a crest of a patient's jawbone and the tissue attachment portion of the collar portion extends above the crest of a patient's jawbone. In some arrangements, the tissue attachment portion extends from the top of the patient's gums to the crest of the patient's jawbone. In other arrangements, the tissue attachment portion extends from the final restoration to the crest of the patient's jawbone.

The tissue attachment zone preferably covers at least 50% of the surface between the crest of the patient's jawbone and the proximal edge of the tissue attachment zone. More preferably, the tissue attachment zone covers at least 75% of this surface. In other applications, the tissue attachment zone covers at least 90% of this surface. Most preferably, the soft tissue attachment zone covers 100% of the surface between the crest of the jawbone and proximal edge of the soft tissue attachment zone.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of this invention will now be described with reference to the drawings of a preferred embodiment which is intended to illustrate and not to limit the invention. The drawings contain the following figures.

DESCRIPTION OF THE PREFERRED EMBODIMENTS

Figure 1A:
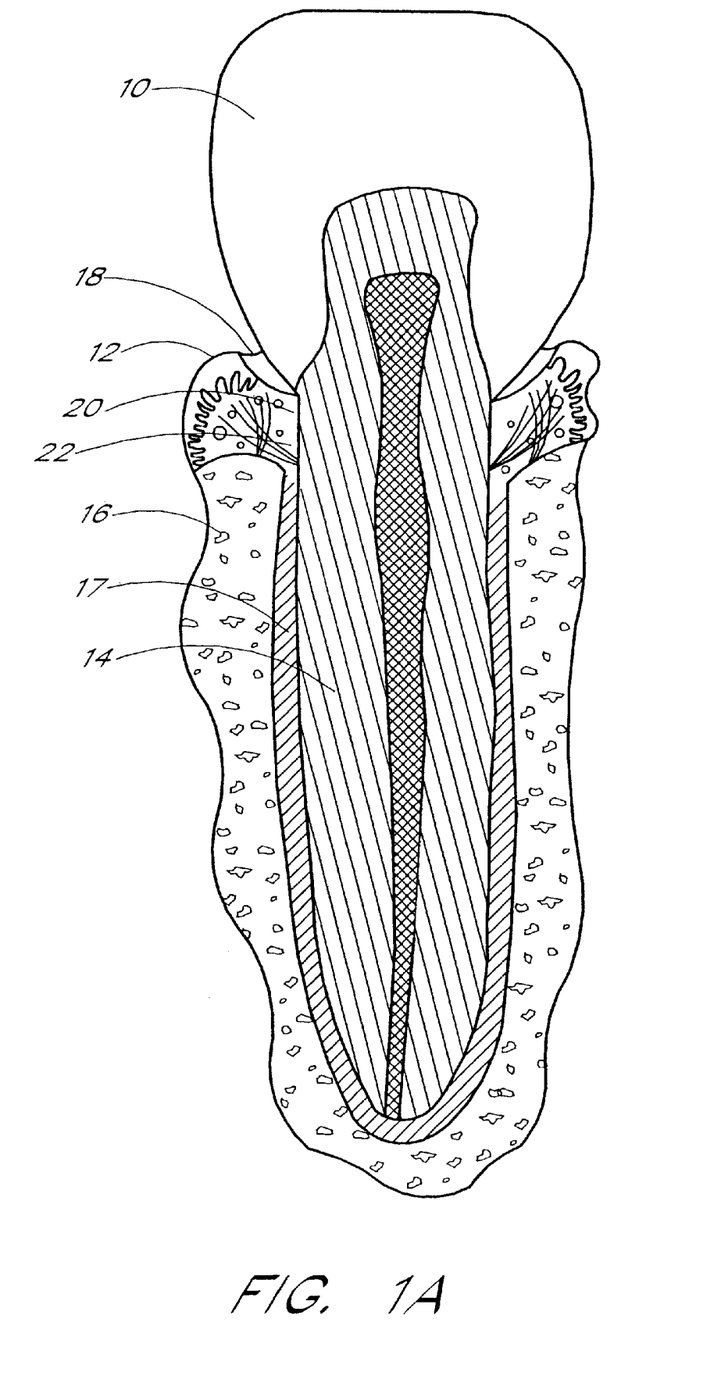
FIG. 1A is a conceptual cross-sectional representation of a facial view of a normal tooth, gum and alveolar bone.
Figure 1B:
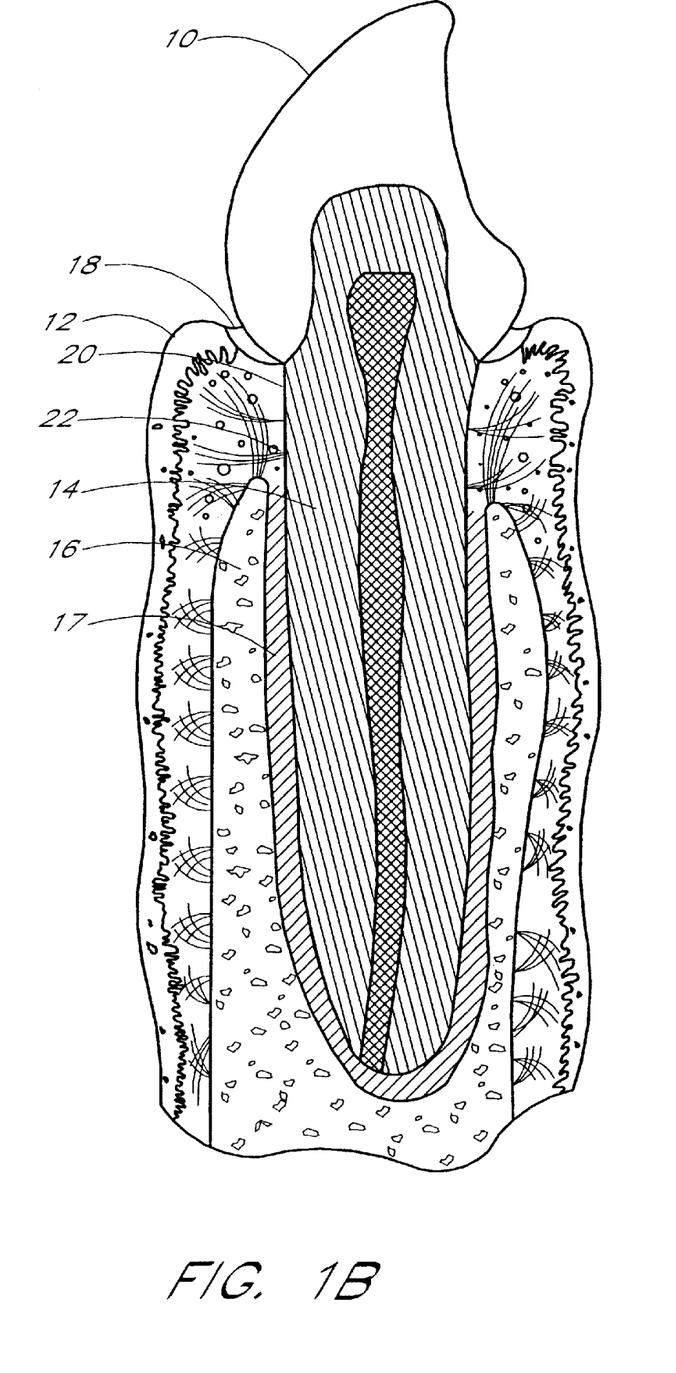
FIG. 1B is a conceptual cross-sectional representation of a mesial view of a normal tooth, gum and alveolar bone.

One aspect of the present invention is the recognition that a healthy human tooth and its gingival counter parts display consistent anatomical structures. For example, FIGS. 1A and 1B are conceptual illustrations of a healthy tooth 10. The soft tissue 12 adjacent the root 14 and coronal to the alveolar bone 16 and periodontal ligament 17 is composed of a gingival sulcus 18 (approximately 1 millimeter deep), an epithelial attachment 20 (approximately 1 millimeter long) and a connective tissue attachment 22 (approximately 1 millimeter long). This distance of approximately 3 millimeters of soft tissue will be referred to as the "biologic width". The biologic width varies from individual to individual but nevertheless generally lies in the range of 2.5 to 3 millimeters.

Figure 2:
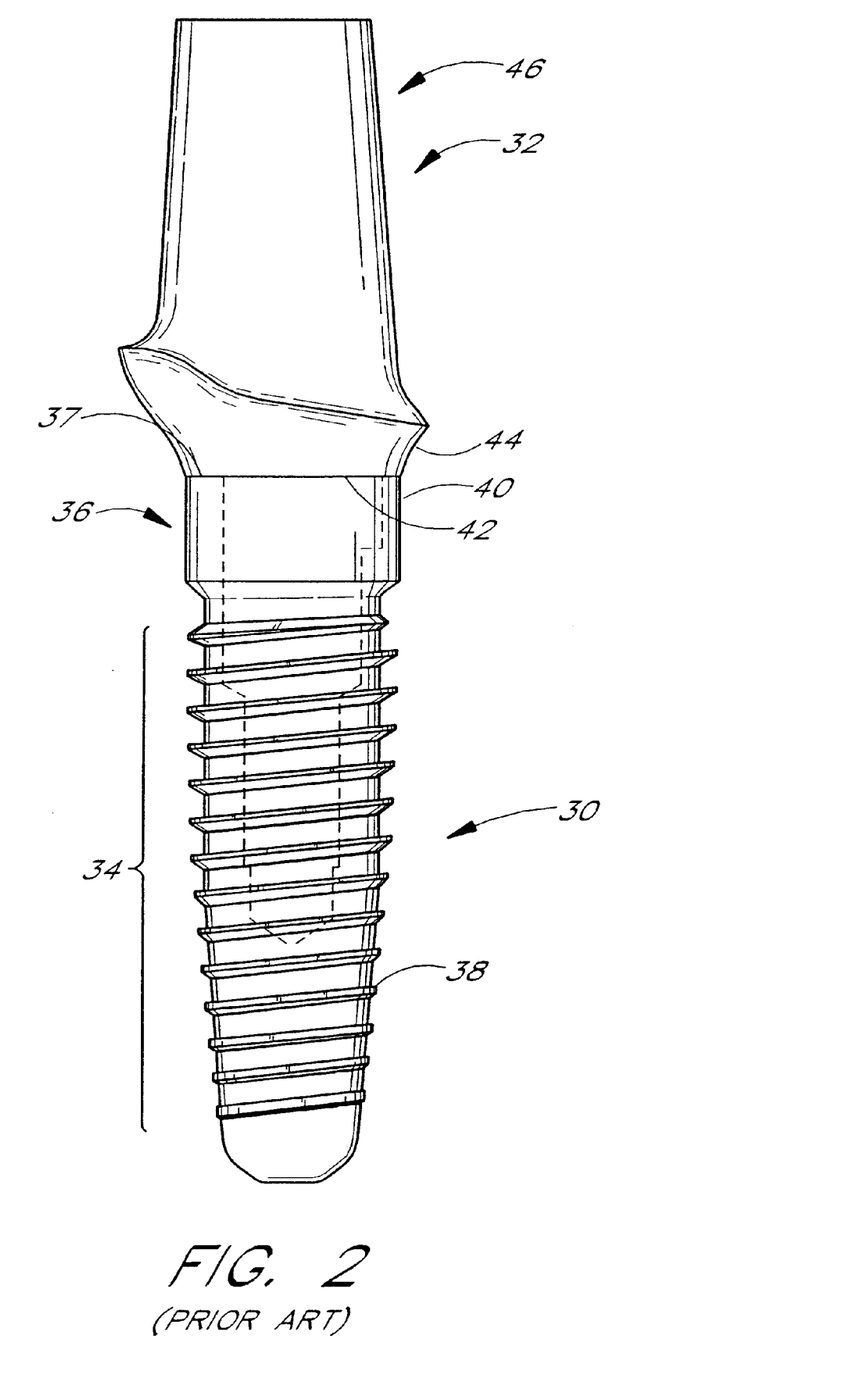
FIG. 2 is a side view of a prior art dental implant and abutment.

FIG. 2 illustrates a dental implant 30 and an abutment 32, which are representative of dental implants and abutments of the prior art. Typically, the dental implant 30 is made from medical grade titanium alloy, although other suitable materials are also used. As is common in the art, the outer surface of the implant 30 includes a body portion 34 and a collar 36. The body portion 34 of the implant 30 is preferably tapered and includes threads 38 that match preformed threads made along the inner surface of the corresponding bore in the patient's jawbone (not shown). In other prior art arrangements, the body portion 34 can be self-tapping, unthreaded and/or cylindrical.

The body portion 34 of the implant 30 typically is roughened to increase the surface area of the body portion 34 so as to promote osteointegration with the alveolar bone. The body portion 34 may be roughened in several different ways. For example, the body portion can be roughed by acid-etching, grit blasting or coating the body portion 34 with a substance such as a calcium phosphate ceramic (e.g., tricalcium phosphate (TCP) and hydroxyapatite (HA)).

In contrast, the collar 36, in particular the coronal portion 40 (i.e., approximately 1–2 millimeters from a top surface 42 of the implant), typically has a smooth machined and/or polished surface. This machined and/or polished surface typically is found on dental implant because the machined and/or polished surface is believed in the art to prevent plaque build up on the implant and allow for easier maintenance.

The abutment 32, which is representative of the prior art, rests one the top surface 42 of the implant 30. The junction between the top surface 42 and the abutment 32 forms a microgap 37. The outer surface of the abutment 32 typically includes a curved transgingival region 44, which is the area of the abutment 32 below the gingival tissue and above the top surface 42 of the implant 30. As with the coronal portion 40 of the implant 30, the transgingival region 44 of the abutment 32 typically has a smooth machined and/or polished surface. The upper region 46 of the abutment 32 is configured to receive a dental restoration (not shown).

Attempts have been made to define and measure surface roughness of prior art abutment and implants (see e.g., Wennerberg, Ann et al., *Design and Surface Characteristics of* 13 *Commercially Available Oral Implant Systems*, JOMI, Vol. 8, No. 6 pages 622–633, (1993)). The Wennerberg article defines two surface roughness parameters: (i) Rt, which is the maximum peak to valley height of the profile of the surface (see page 623) and (ii) Ra, which is the mean value of the peak to valley distance. Using the Wennerberg definitions, the smooth machined and/or polished surface of prior art abutments and implants have a Rt of approximately 10 microns or less and Ra of approximately 0.6 microns or less.

Figure 3A:
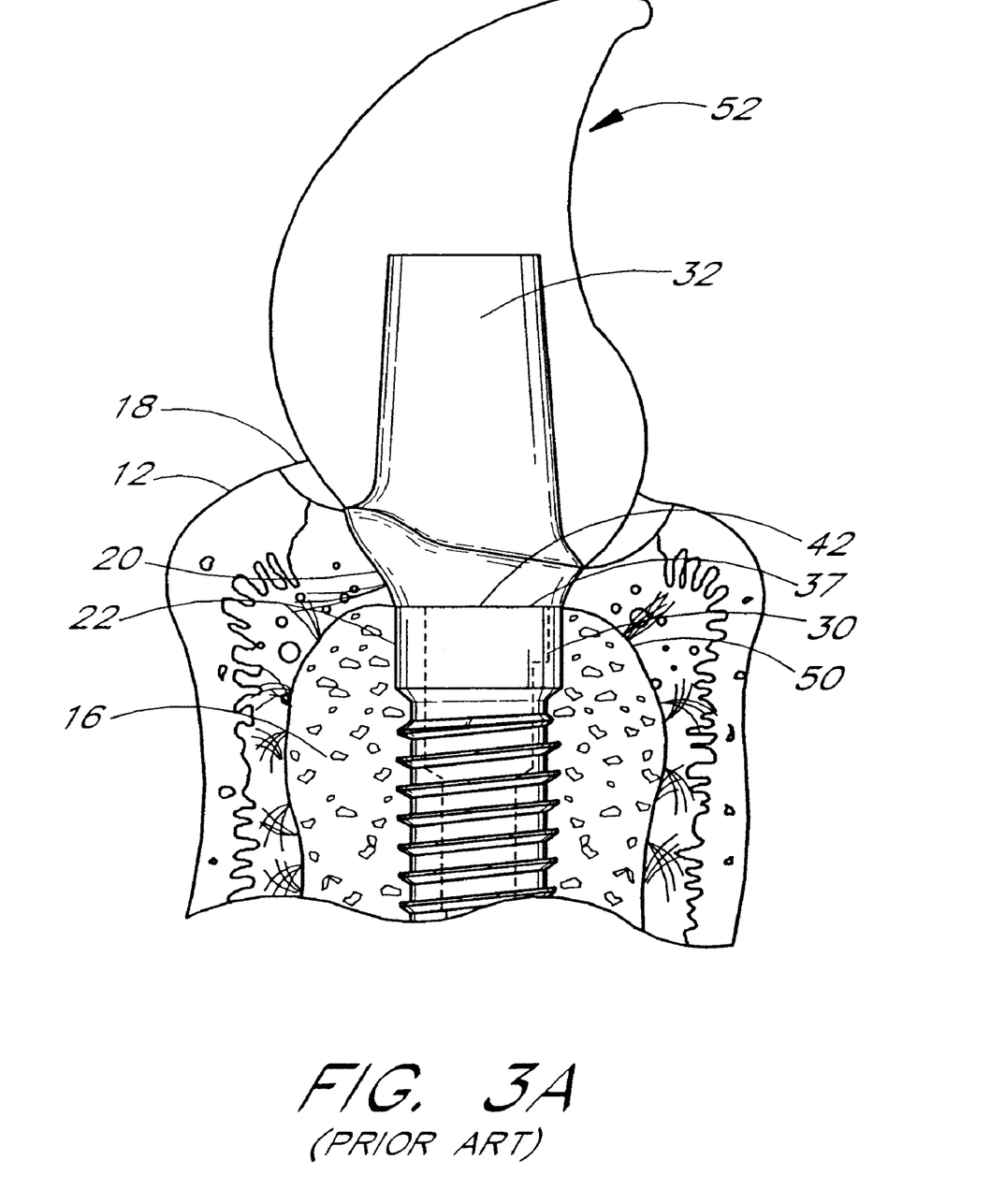
FIG. 3A is a side view of the dental implant and abutment of FIG. 2 installed into a patient's jawbone.

FIG. 3A is a conceptual illustration of the implant 30 and abutment 32 of FIG. 2 installed in a patient's mouth. Initially, the top surface 42 of the implant 30 lies flush or slightly below or above the crest 50 of the jawbone. The soft tissue 12 extends above the jawbone 16 along side the abutment 32 and a final prosthesis 52, which is attached to the abutment 32. As mentioned above, the soft tissue 16 is composed of a gingival sulcus 18, an epithelial attachment 20 and a connective tissue attachment 22.

Figure 3B:
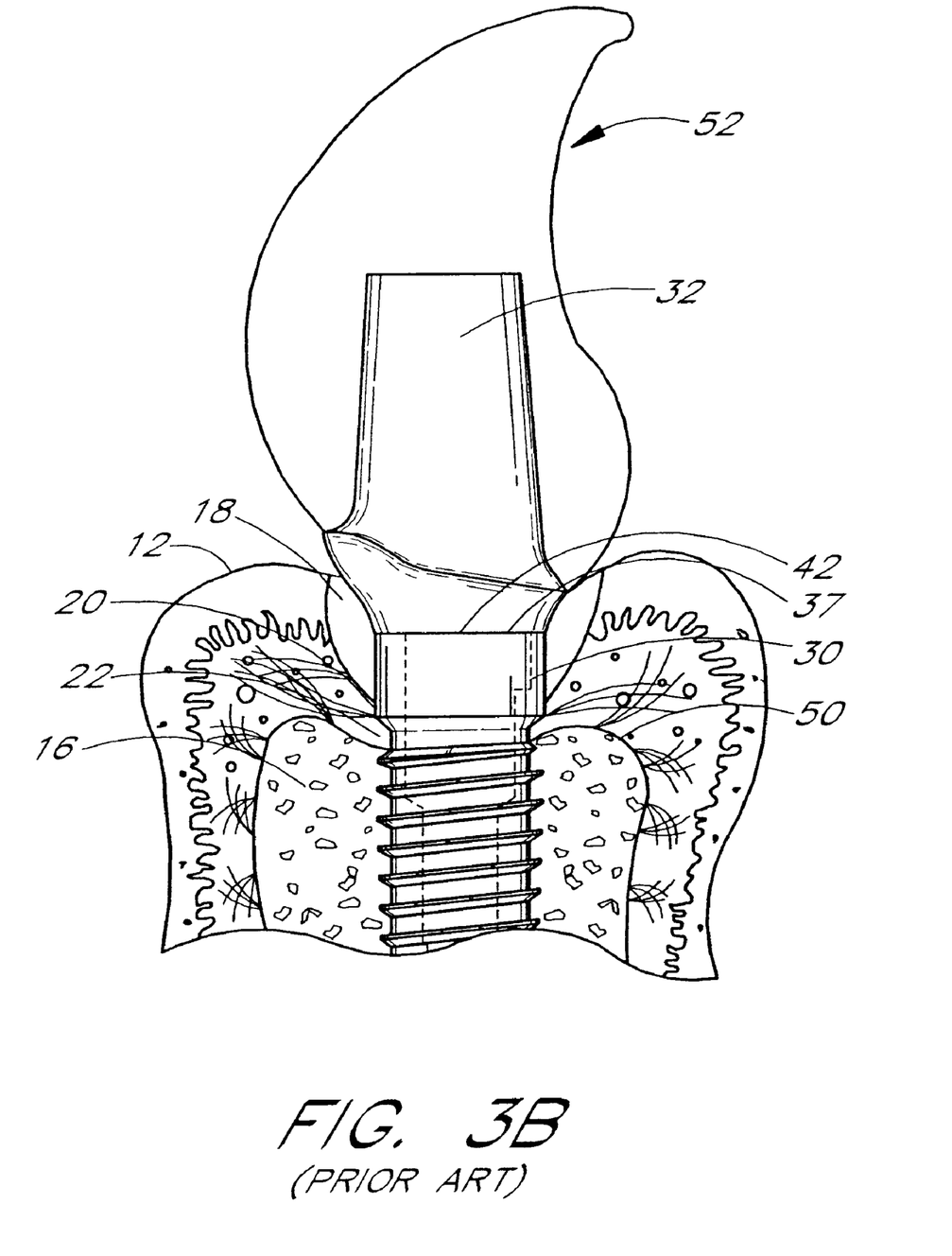
FIG. 3B is a side view of the dental implant and abutment of FIG. 2 installed into a patient's jawbone after a period of time.

Applicant has observed that the connective tissue attachment 22 does not to attach the smooth, machined and/or polished surfaces of the collar 36 and the abutment 32. The gingival connective tissue 22 must attach to a biocompatible surface to prevent the apical proliferation of the epithelial attachment. As shown in FIG. 3B, over time the body responds to the lack of tissue attachment surface by reabsorbing the bone tissue to expose the biocompatible, roughened surfaces of the lower portions of the implant 30 so that the connective tissue 22 can attach to the implant. This produces a gingival sulcus that is approximately 4–5 millimeters deep (as compared to the normal 1 millimeter) and the epithelial attachment is often 3–4 millimeters long (as compared to the normal 1 millimeter). The increased sulcus depth and the longer epithelial attachment dimensions often leads to esthetic and/or maintenance problems with prior art dental implants and abutments. Moreover, the alveolar bone loss can destabilize the gingival tissues.

Applicant has also observed that the body's defense mechanism also tends to provide a 2–3 millimeter biological width of soft tissue between the microgap 37 and the crest 50 of the jawbone 16. Therefore, the body tends to reabsorb the bone tissue as shown in FIG. 3B until an adequate distance for connective tissue and epithelial attachment lies between the bone 16 and the microgap 37.

Figure 4:
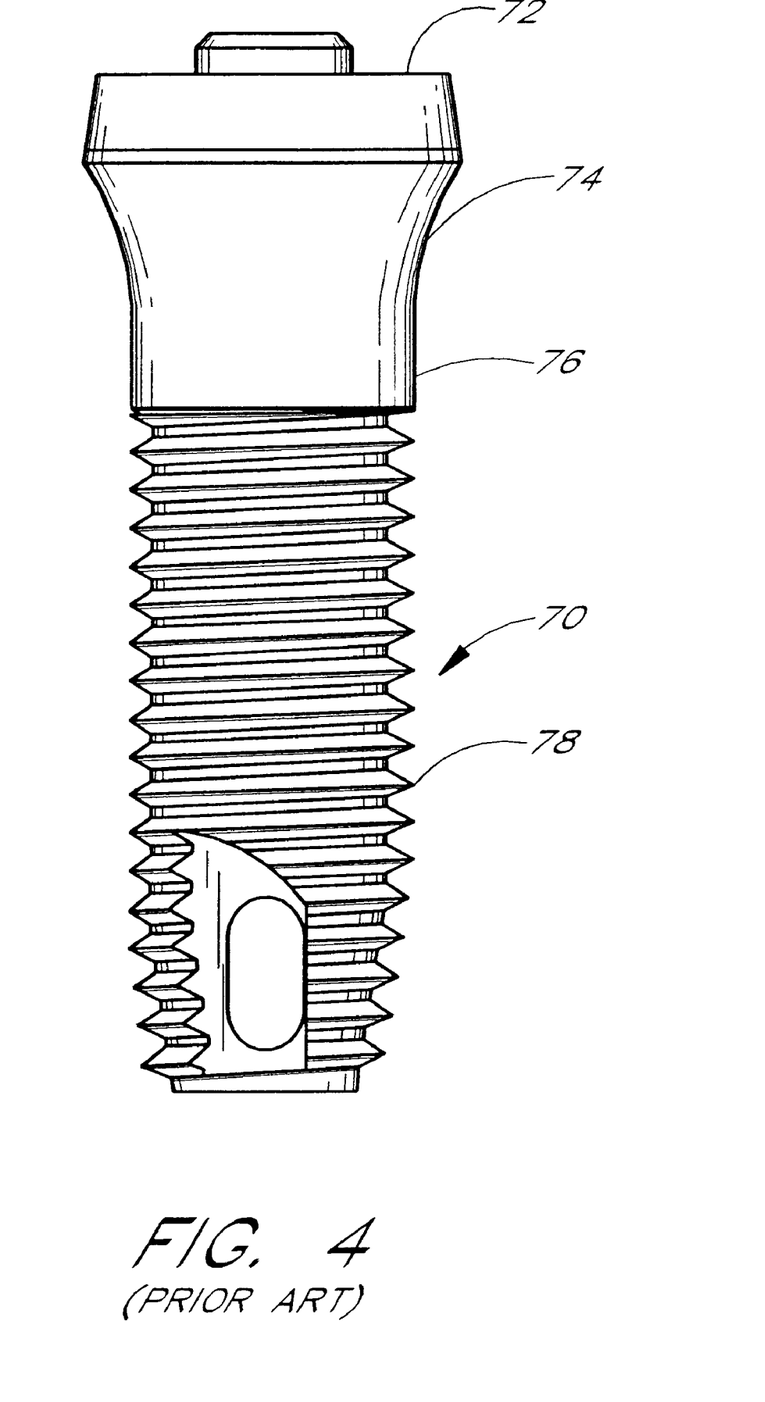
FIG. 4 is a side view of another prior art dental implant.

FIG. 4 is representative of another type of prior art implant. With this implant 70, the top surface 72 of the implant is configured to lie significantly above the crest of the alveolar bone. As such, the implant 70 includes a curved transgingival region 74 that is integrally formed with the collar 76 and implant body 78. The curved transgingival region 74 typically has a smooth machined and/or polished surface. This smooth machined and/or polished surface extends through the collar 76 and to approximately 1 millimeter below the alveolar crest. Although the junction (i.e., the top surface 72) between an abutment (not shown) and the implant 70 lies above the alveolar crest, the increased biologic width dimension and alveolar bone loss described above are still observed because of the smooth surfaces in the transgingival region 74 and the collar 76 extend approximately 1 millimeter below the alveolar crest.

Figure 5A:
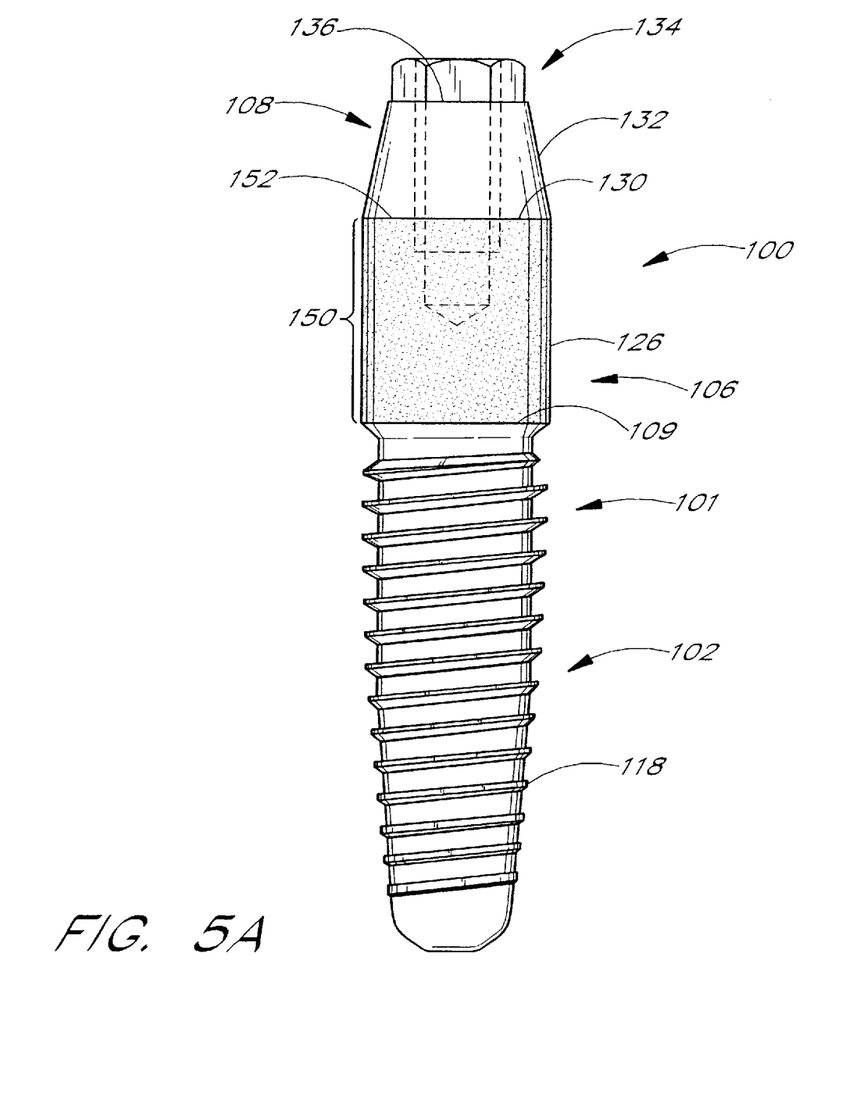
FIG. 5A is a side view of a dental implant having certain feature and advantages according to the present invention.
Figure 5B:
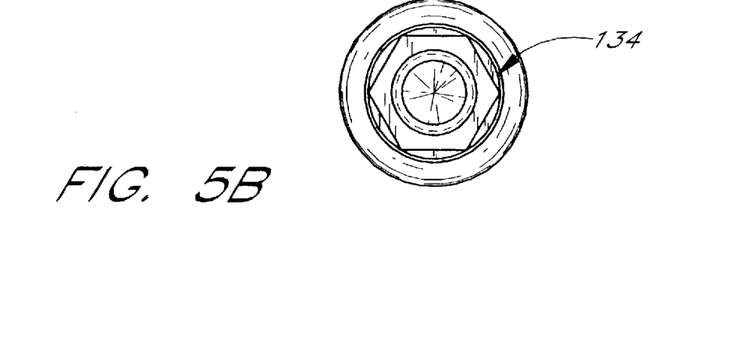
FIG. 5B is a top plan view of the dental implant of FIG. 5A.

FIG. 5A–B illustrate an arrangement of a dental implant 100 having certain features and advantages in accordance with the present invention. The implant 100 is preferably made of a dental grade titanium alloy, although other suitable materials can be used.

As best seen in FIG. 5A, the implant 100 preferably includes an implant body 101, which preferably includes a lower portion 102, a collar 106, and abutment portion 108. The body portion 102 of the implant 100 is preferably tapered and includes threads 118 that match preformed threads made along the inner surface of a bore in the patient's jawbone (not shown). However, it should be appreciated that the body portion 102 can be configured so as to be self-tapping. It should also be appreciated that although the illustrated body portion 102 is tapered or conical, the body portion 102 could also be substantially cylindrical. The body portion 102 can also be unthreaded if the surgeon prefers to use an unthreaded implant.

The body portion 102 preferably has a roughened surface, which increases the surface area of the body portion 102. The increased surface area promotes osseointegration, as is well known in the art. The body portion can be roughened in several different manners, such as, for example, acid-etching, grit blasting, and/or machining. Alternatively, the body portion 102 can be coated with a substance that increases the surface area of the body portion 102. Calcium phosphate ceramics, such as tricalcium phosphate (TCP) and hydroxyapatite (HA), are particularly suitable materials.

As best seen in FIG. 5A, the collar 106 preferably lies above (i.e., proximal) the body portion 102 and is integrally connected to the body portion 102. The illustrated collar 106 is substantially cylindrical and is defined in part by a side wall 126, which preferably extends in a substantially vertical direction. A collar/body junction 109 represents the boundary between the body portion 102 and the collar 106. The collar 106 has a height that is preferably greater than 2 millimeters. More preferably, the collar 106 has a height of approximately 4 millimeters. In a modified embodiment, the side wall 126 of the collar 106 can be conicaly flaring or narrowing in a straight or curved manner. The side walls 126 can also be curved so as to match or closely approximate the contours of a natural tooth. In a similar manner, the collar 106 can also have a non-round cross section.

The abutment 108 preferably is integrally connected to the collar 106. The illustrated implant 100 is configured such that, when the implant 100 is installed into the patient's jawbone, the implant/abutment junction 130 (i.e., the boundary between the collar 106 and the abutment 108) lies approximately 2–4 millimeters coronal to the crest of the jawbone. Preferably, the collar/body junction 109 lies approximately 1 millimeter below the crest of the jawbone.

In the illustrated arrangement, the surgeon can vary the position of the implant/abutment junction 130 with respect to the alveolar crest. For example, the implant/abutment junction 130 can be positioned above the alveolar crest without exposing the threads 118 of the body region 102. Alternatively, as described above, the surgeon can position the implant/abutment junction 130 two millimeters above the alveolar crest for aesthetics. In yet another alternative arrangement, the surgeon can submerge the collar 106 into the jawbone such that the collar/body junction 109 lies as much as approximately 1 millimeter or more below the alveolar crest.

It should, however, be noted that several advantages of the present invention can be achieved with a collar having dimensions that are smaller or larger than the illustrated arrangement. However, the illustrated arrangement is preferred because it best allows for the flexibility described above.

The abutment 108 preferably includes a tapered body 132. The tapered body 132 preferably is configured to extend above the gingival tissues of the patient. A hexagonal boss 134 is preferably provided at the top of the tapered body 132. The hexagonal boss 134 can be used with a tool (not shown), such as, for example a wrench to screw the implant 100 into the patient's jawbone. Although the illustrated arrangement includes a hexagonally shaped boss 134, the implant 100 may include a boss or recess formed in a variety of other suitable symmetric or non-symmetric shapes giving consideration to the goal of transmitting torque. In modified arrangements, the abutment 108 can be formed without a protrusion or recess and instead include flattened sides or grooves on the side of the abutment for transmitting torque from a tool to the implant 100. In yet another modified arrangement, the abutment 108 can be formed without a protrusion or recess and the dental practitioner can instead use a pair of pliers or similar tool to grab and twist the abutment 108 directly.

The illustrated abutment 108 preferably also includes a central bore 136, which is preferably threaded. The bore is configured to receive a bolt (not shown), which can be used to secure various dental components, such as, for example, a healing cap and/or a final restoration to the abutment 108. Of course, those of skill in the art will appreciate that the abutment 108 can be configured without the central bore 136. In such an arrangement, dental components can be attached to the abutment 108 using, for example, dental cement or other suitable adhesives.

The implant 100 preferably includes a soft tissue attachment zone, which is indicated generally by the reference number 150. The soft tissue attachment zone 150 is preferably roughened so as to promote attachment of connective soft tissues. The soft tissue attachment zone 150 is at least about twice as rough as the smooth machined and/or polished surfaces of prior art abutments in the transgingival region. More preferably, the soft tissue attachment zone 150 is at least about five times rougher than these smooth machined and/or polished surfaces. In some embodiments, the soft tissue attachment zone 150 is at least about ten times rougher than these smooth machined and/or polished surfaces. The soft tissue attachment zone 150 of the implant 100 can be formed in a variety of ways, such as, for example, mechanical etching (e.g., machining, grinding, grit blasting), chemical etching (e.g., acid-etching), electric discharge machines, laser etching, and/or application of textured surfaces (e.g., calcium phosphate ceramics, such as tricalcium phosphate (TCP) and hydroxyapatite (HA)).

When the implant 100 is installed in the patient's mouth, the soft tissue attachment zone 150 preferably extends from the alveolar crest to at least approximately 2 millimeters above the alveolar crest. Preferably, the soft tissue attachment zone 150 extends at least approximately 3 millimeters above the alveolar crest. In other embodiments, the soft tissue attachment zone 150 extends at least approximately 4 millimeters above the alveolar crest. More preferably, the soft tissue attachment zone 150 extends from the alveolar crest to the end of the transgingival region. Most preferably, the soft tissue attachment zone 150 extends from the alveolar crest to the final restoration. Below the alveolar crest, the soft tissue attachment zone 150 preferably extends to the body portion 102.

In the illustrated arrangement, the implant 100 is configured such that the collar/body junction 109 preferably lies about 1 millimeter below the alveolar crest. As such, the soft tissue attachment zone 150 preferably extends at least approximately 2 millimeters above the collar/body junction 109. More preferably, the soft tissue attachment zone 150 extends at least approximately 3 millimeters above the collar/body junction 109 Most preferably, the soft tissue attachment zone 150 lies at least approximately 4 millimeters above the collar/body junction 109. In modified arrangements, the location of the implant/abutment junction 130 and the collar/body junction 109 with respect to the alveolar crest can be modified. In such, arrangements the dimensions of the soft tissue attachment zone 150 can be adjusted accordingly. As mentioned above, when the implant 100 is installed in the patient's mouth, the soft tissue attachment zone 150 preferably also extends below the alveolar crest to the body portion 102, which preferably has a surface configured for promoting osseointegration as described above.

The soft tissue attachment zone 150 preferably extends at least 300 degrees around the circumference of the implant 100. More preferably, the soft tissue attachment zone 150 extends at least 330 degrees around the circumference of the implant. In other embodiments, the soft tissue attachment zone 150 extends 360 degrees around the circumference of the implant 100 as illustrated in FIG. 5A.

The soft tissue attachment zone 150 preferably covers at least 50% of the surface between the alveolar crest and the proximal edge of the soft tissue attachment zone 150. More preferably, the soft tissue attachment zone 150 covers at least 75% of this surface. In other applications, the soft tissue attachment zone 150 covers at least 90% of this surface. Most preferably, as shown in FIG. 5A, the soft tissue attachment zone 150 covers 100% of the surface between the alveolar crest and proximal edge of the soft tissue attachment zone 150.

Figure 5C:
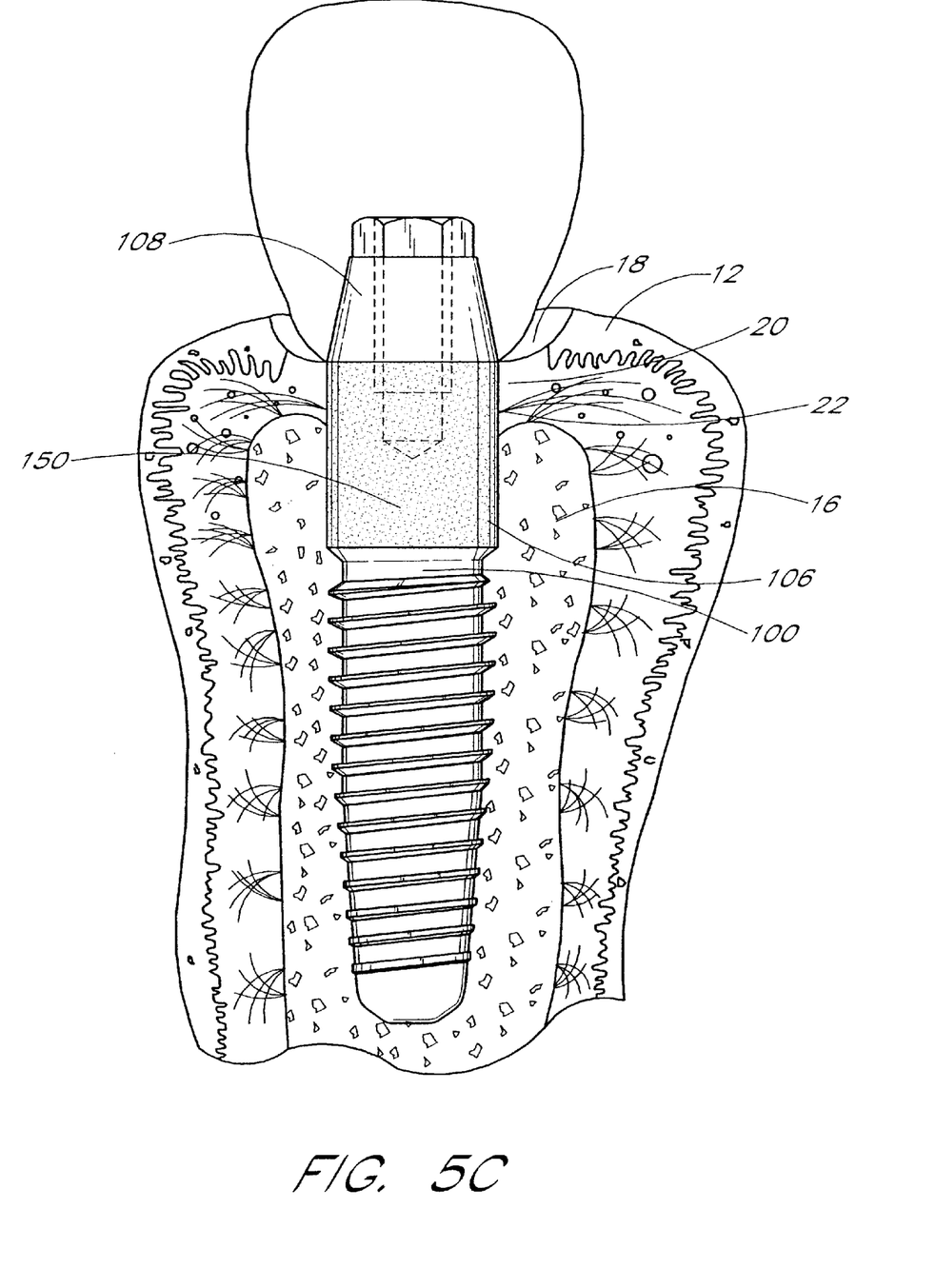
FIG. 5C is a facial view of the dental implant and abutment of FIG. 5A installed into a patient's jawbone.
Figure 5D:
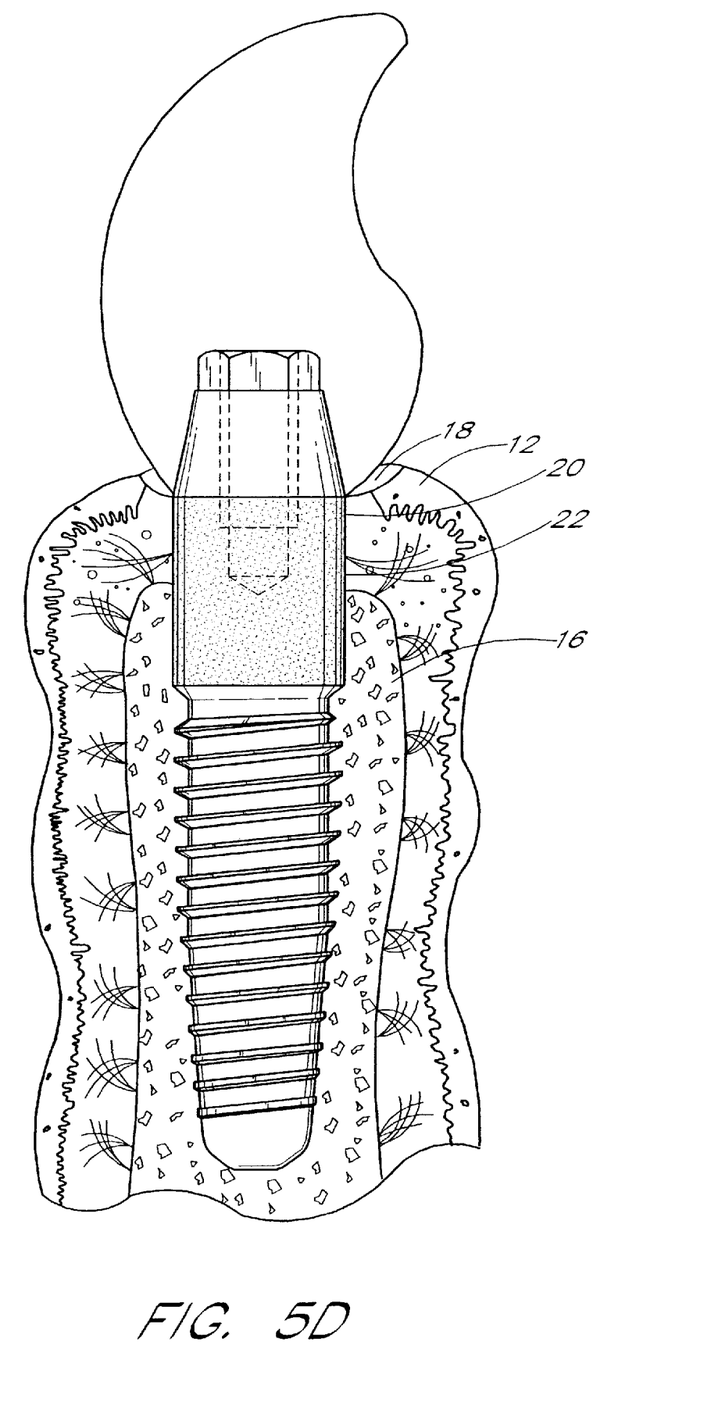
FIG. 5D is a mesial view of the dental implant and abutment of FIG. 5A installed into a patient's jawbone.

As shown in FIGS. 5C and 5D, the soft tissue attachment zone 250 of the implant 100 described above allows the connective tissue 22 to attach to the collar 106 of the implant 100. As such, as the patient's mouth heals, the structure of the soft tissue coronal to the alveolar bone 16 resembles that of a natural tooth. That is, the soft tissue is composed of a gingival sulcus 18 (approximately 1 millimeter deep), an epithelial attachment 20 (approximately 1 millimeters long) and a connective tissue attachment 22 (approximately 1 millimeters long). This reduces bone loss and improves the aesthetics of the restoration.

It should be noted that the doctor typically modifies the abutment portion 108 of the implant 100 by machining it with a burr as shown in FIGS. 5C and 5D. In this manner, the abutment portion can be reduced in size to produce a smooth transition to the center of the implant. Of course, in other arrangements, the abutment portion 108 can be configured such that the doctor need not be modified.

Figure 6:
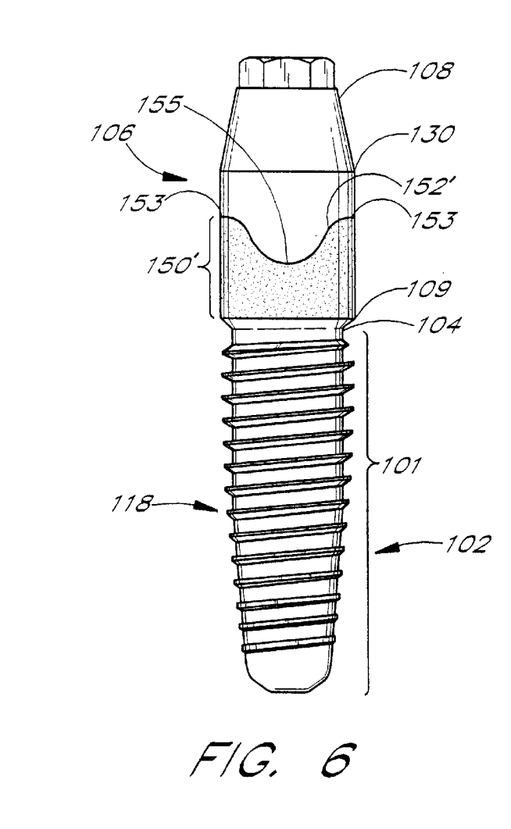
FIG. 6 is a side view of a modified arrangement of a dental implant having certain feature and advantages according to the present invention.

In the arrangement described above in connection with FIG. 5A, a top edge 152 of the soft tissue attachment zone 150 is generally flat or planar. FIG. 6 illustrates a modified arrangement wherein the top edge 152' of the soft tissue attachment zone 150' is curved or scalloped shaped with approximately two peaks 153 and two valleys 155. In this arrangement, the top edge 152' preferably follows or at least closely approximates the general shape of the naturally occurring contours of a patient's gums and alveolar crest. Such an arrangement is more aesthetic and reduces plaque formation about the gumline.

Figure 7A:
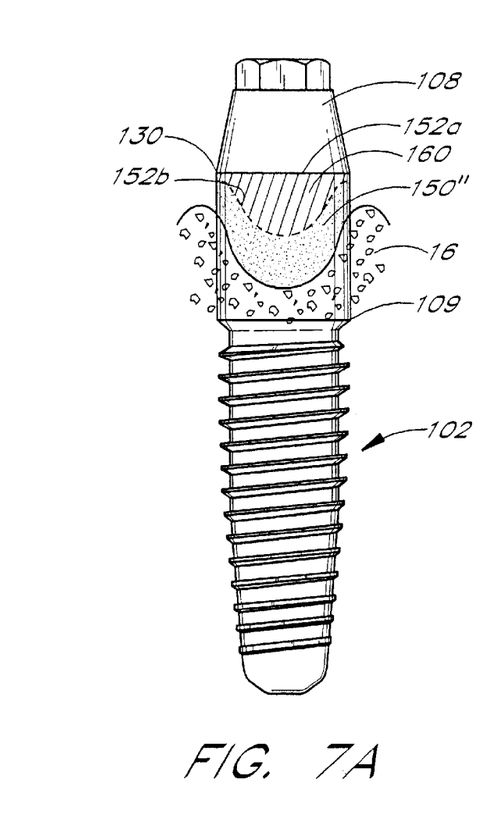
FIG. 7A is side view of another modified arrangement of a dental implant having certain features and advantages according to the present invention.
Figure 7B:
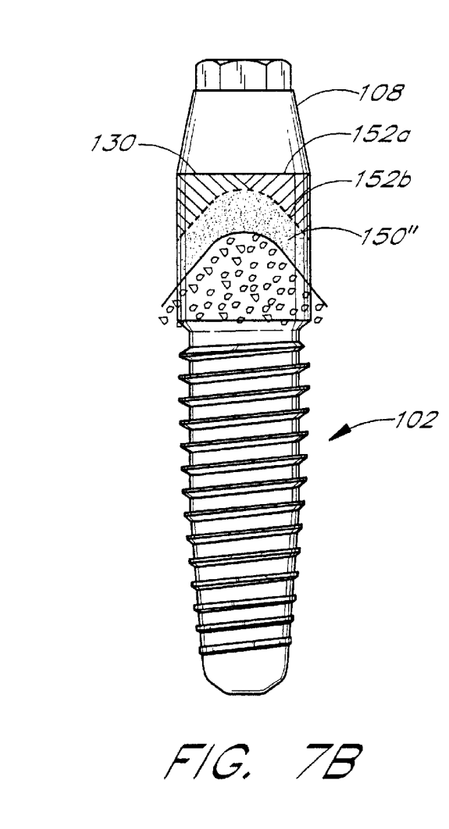
FIG. 7B is a front view of the dental implant of FIG. 7A rotated 90 degrees.

In yet another modified arrangement, the soft tissue attachment zone 150 is configured such that it can be customized by the surgeon or dentist to conform to the biologic and esthetic contours of a unique patient's gums and alveolar crest. As shown in FIG. 7A, the implant 100 preferably is installed into the patient's jawbone 16. Initially, the top edge 152a of the soft tissue attachment zone does not conform to the curved or scalloped shape of the patient's gums and the alveolar crest. Using a suitable tool (not shown), such as, for example, an abrasive tool or an ultrasonic cleaning instrument, the surgeon or dentist can smooth out upper portions 160 of the soft tissue attachment zone 150" to modify the shape of the top edge 152a of the soft tissue attachment zone 150". In this manner, the soft tissue attachment zone 150 can be formed such that the top edge 152b extends substantially uniformly at least 2–4 millimeters above the scalloped alveolar crest. Preferably, after smoothing, the upper portions 160 have a surface roughness that is similar to that of a natural tooth adjacent the gingival sulcus.

It should be appreciated that although in the arrangements described above the abutment 108 is integrally formed with the implant 100, certain features and advantages of the present invention can be achieved in an arrangement wherein the abutment is formed as separate piece (i.e., a two-piece system) that can be attached to the implant before, during or after surgery. In such arrangements, the abutment can be attached to the implant in a variety of ways, such as, for example, by a bolt that extends through a central bore formed in the abutment and the implant and/or by the application of adhesives.

Figure 8:
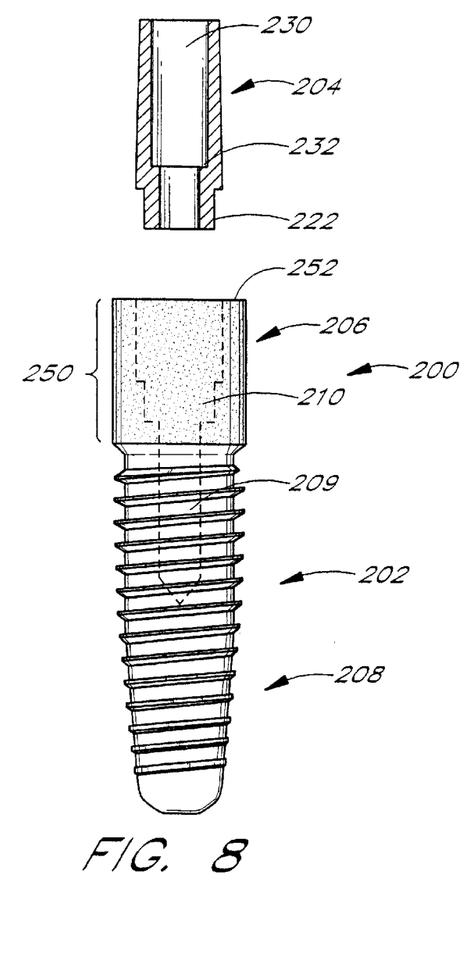
FIG. 8 is a side view of yet another modified arrangement of a dental implant having certain features and advantages according to the present invention.

FIG. 8 illustrates one arrangement of such a dental implant 200 having certain features and advantages according to the present invention. In this arrangement, the implant 200 is a two piece implant that includes an implant body 202 and an abutment 204. The implant body 202 preferably includes a lower portion 208 configured as described above. The implant body 202 preferably also includes a threaded bore 209. Above the threaded bore 209 lies a post receiving chamber 210, which in some arrangements can include anti-rotational features, such as, for example, flat sides, grooves, and or indentations.

A collar 206 lies above the implant body 202 and is preferably configured as described above. The collar 206 supports the abutment 204, which lies on top of the implant body 202. In the illustrated arrangement, the abutment 204 is configured to fit, at least partially within the collar 206. Specifically, in the illustrated arrangement, the abutment includes a post 222 that is configured to fit within the post receiving chamber 210. As mentioned above, the post receiving chamber 210 can include anti-rotational features. If the post receiving chamber 210 includes such anti-rotational features, the post 222 preferably includes corresponding structures so as to prevent the abutment 204 from rotating with respect to the implant body 202.

The abutment 204 preferably includes a central bore 230 with a shoulder 232. The central bore 230 and shoulder 232 are configured to receive a bolt (not shown). The bolt, in turn, is configured such that one end of the bolt extends through the abutment 204 and into the threaded bore 209 of the implant body 208. In such a manner, the bolt can be used to secure the abutment 204 to the implant body 208.

As with the previous arrangements, the implant 200 preferably includes a soft tissue attachment zone 250. When the implant 200 is installed in the patient's mouth, a top edge 252 of the soft tissue attachment zone 250 preferably extends at least approximately 2 millimeters above the alveolar crest. More preferably, the soft tissue attachment zone extends at least approximately 3 millimeters above the alveolar crest. Most preferably, the soft tissue attachment zone extends at least approximately 4 millimeters zone above the alveolar crest. Moreover, the soft tissue attachment zone 250 preferably extends completely from the top surface 252 to the implant body 208. In a modified arrangement of the implant 200, the top edge of the soft tissue attachment zone can be curved or scalloped shaped as described above.

Figure 9A:
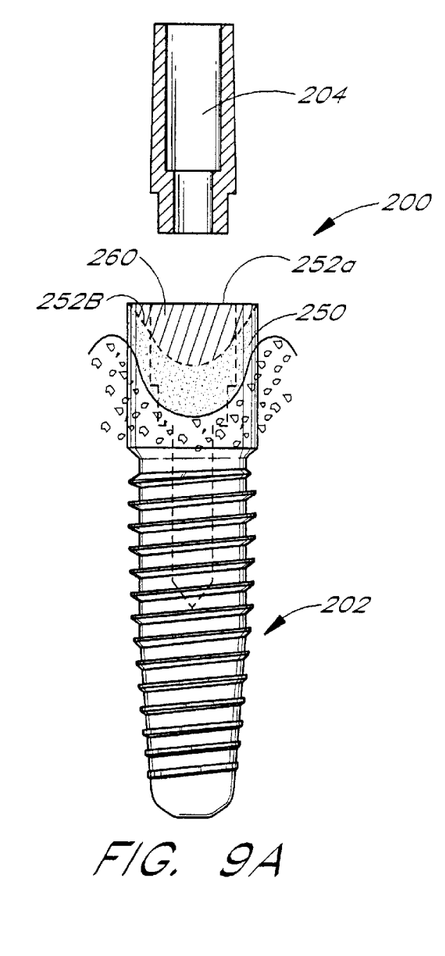
FIG. 9A is side view of still yet another modified arrangement of a dental implant having certain features and advantages according to the present invention.
Figure 9B:
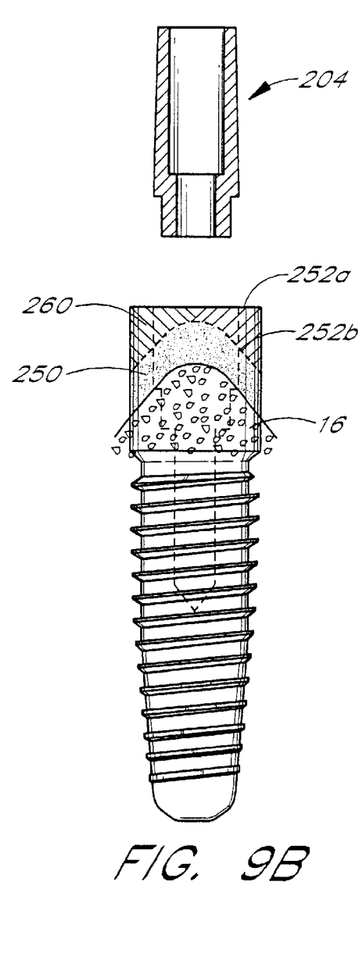
FIG. 9B is a front view of the dental implant of FIG. 9A rotated 90 degrees.

FIGS. 9A and 9B illustrate another modified arrangement of a two-piece dental implant system. In this arrangement, the dental implant body 202 and the abutment 204 are arranged substantially as described above. However, in this arrangement, the soft tissue attachment zone 250 is configured such that it can be customized by the surgeon or dentist to conform to the biologic and aesthetic contours of the patient's gums and alveolar crest. As shown in FIG. 9A, the implant 200 preferably is installed into the patients jawbone 16. Initially, the top edge of the 252a of the soft tissue attachment zone does not conform to the curved or scalloped shape of the patient's gums and the alveolar crest. Using a suitable tool (not shown), such as, for example, an ultrasonic cleaning instrument, the surgeon or dentist can smooth out upper portions 260 of the soft tissue attachment zone 250 to modify the shape of the top edge 252a of the soft tissue attachment zone 250. In this manner, the soft tissue attachment zone 250 can be formed such that the top edge 252b extends substantially uniformly at least 2–4 millimeters above the scalloped alveolar crest. Preferably, after smoothing, the upper portions 260 have a surface roughness that is similar to that of a natural tooth adjacent the gingival sulcus.

In a modified arrangement, the surgeon or dentist can customize the shape of the top edge 252 by machining away top portions of the abutment portion 108 and collar 106 with, for example, a burr. In this manner, the surgeon or dentist can form a continuous smooth transition from the implant to the dental restoration.

A dental implant installing method having certain features and advantages according to present invention will now be described. This method preferably comprises placing an analog of the abutment portion 108 of the implant 100 onto a cast of the patient's mouth at a desired position. The analog temporarily attached to the cast with, by way of example, wax or an adhesive. A surgical stent is formed around the analog with, by way of example, self cure acrylic or other similar material. This indexes the stent to the adjacent teeth in the model and the patient mouth. The stent is taken to the patient's mouth for surgery and used as a surgical guide.

A pilot hole through the stent and into the tissue and the bone. The stent is then removed. A tissue punch guide is placed in the pilot hole and a tissue punch is used to cut a hole through the tissue. The hole preferably has a diameter and shape that closely corresponds to the diameter and shape of the collar portion 106 of the dental implant 100. A tissue plug (i.e., the tissue corresponding to the hole) is then removed. The surgeon can add a surgical flap (i.e., an incision), which preferably bisects the hole through the tissue, depending on the surgeon's assessment of the size and shape of the underlying jawbone.

The implant is then installed through the hole. If an incision was made, the tissue is sutured shut. The method provides for a snug seal of the gum tissue around the implant 100. In contrast, if an incision alone is made, the gum tissue may not conform to the implant when it is sutured back together around the implant and epithelium can grow down the gaps around the implant.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

We claim:

1. A method for installing a dental prosthesis into a patient's mouth, the method comprising the steps of:
    providing a dental implant comprising a body portion at a distal end of the dental implant, an abutment portion at a proximal end of the dental implant and a collar portion located between the body portion and the abutment portion and including an outer surface with a roughened portion;
    installing the dental implant into the patient's jawbone such that the body portion lies substantially beneath a crest of a patient's jawbone and the roughened portion of the collar portion extends above the crest of a patient's jawbone; and
    smoothing an upper portion of the roughened surface.

2. The method of claim 1, wherein the step of installing the dental implant into the patient's jawbone such that the body portion lies substantially beneath a crest of a patient's jawbone and the roughened portion of the collar portion extends above the crest of a patient's jawbone further includes the step of extending the roughened portion at least approximately 2 millimeters above the crest of the patent's jawbone.

3. The method of claim 1, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 3 millimeters above the crest of the patient's jawbone.

4. The method of claim 1, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 4 millimeters above the crest of the patient's jawbone.

5. The method of claim 1, wherein the step of providing a dental implant comprising a body portion at a distal end of the dental implant, an abutment portion at a proximal end of the dental implant and a collar portion located between the body portion and the abutment portion and including an outer surface with a roughened portion further includes integrally forming the collar portion with the body portion.

6. The method of claim 1, further comprising attaching the abutment portion to the collar with a bolt.

7. A method for installing a dental prosthesis into a patient's mouth, the method comprising the steps of:
    providing a dental implant comprising a body portion at a distal end of the dental implant, an abutment portion at a proximal end of the dental implant and a collar portion located between the body portion and the abutment portion and including an outer surface with a roughened portion;
    installing the dental implant into the patient's jawbone such that the body portion lies substantially beneath a crest of a patient's jawbone and the roughened portion of the collar portion extends above the crest of a patient's jawbone; and
    smoothing an upper portion of the roughened surface, wherein the step of smoothing an upper portion of the roughened portion includes smoothing the upper portion of the roughened portion such that a top edge of the roughened portion generally matching a contour the crest of the patient's jawbone.

8. The method of claim 7, wherein the step of installing the dental implant into the patient's jawbone such that the body portion lies substantially beneath a crest of a patient's jawbone and the roughened portion of the collar portion extends above the crest of a patient's jawbone further includes the step of extending the roughened portion at least approximately 2 millimeters above the crest of the patient's jawbone.

9. The method of claim 7, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 3 millimeters above the crest of the patient's jawbone.

10. The method of claim 7, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 4 millimeters above the crest of e patient's jawbone.

11. The method of claim 7, wherein the step of providing a dental implant comprising a body portion at a distal end of the dental implant, an abutment portion at a proximal end of the dental implant and a collar portion located between the body portion and the abutment portion and including an outer surface with a roughened portion further includes integrally forming collar portion with the body portion.

12. The method of claim 7, further comprising attaching the abutment portion to the collar with a bolt.

13. A method for installing a dental prosthesis into a patient's mouth, the method comprising the steps of:
    providing a dental implant comprising a body portion at a distal end of the dental implant, an abutment portion at a proximal end of the dental implant and a collar portion located between the body portion and the abutment portion and including an outer surface with a roughened portion;
    installing the dental implant into the patient's jawbone such that the body portion lies substantially beneath a crest of a patient's jawbone and the roughened portion of the collar portion extends above the crest of a patient's jawbone; and smoothing an upper portion of the roughened surface, wherein the step of smoothing an upper portion of the roughened portion includes smoothing the upper portion until the upper portion has a surface as approximately smooth as a surface of a natural tooth above a patient's gumline.

14. The method of claim 13, wherein the step of installing the dental implant into the patient's jawbone such that the body portion lies substantially beneath a crest of a patient's jawbone and the roughened portion of the collar portion extends above the crest of a patient's jawbone further includes the step of extending the roughened portion at least approximately 2 millimeters above the crest of the patient's jawbone.

15. The method of claim 13, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 3 millimeters above the crest of the patient's jawbone.

16. The method of claim 13, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 4 millimeters above the crest of the patient's jawbone.

17. The method of claim 13, wherein the step of providing a dental implant comprising a body portion at a distal end of the dental implant, an abutment portion at a proximal end of the dental implant and a collar portion located between the body portion and the abutment portion and including an outer surface with a roughened portion further includes integrally forming the collar portion with the body portion.

18. The method of claim 13, further comprising attaching the abutment portion to the collar with a bolt.

19. A method for installing a dental prosthesis into a patient's mouth, the method comprising the steps of:

providing a dental implant comprising a body portion at a distal end of the dental implant, an abutment portion at a proximal end of the dental implant and a collar portion located between the body portion and the abutment portion and including an outer surface with a roughened portion;

installing the dental implant into the patient's jawbone such that the body portion lies substantially beneath a crest of a patient's jawbone and the roughened portion of the collar portion extends above the crest of a patient's jawbone;

removing an upper portion of the roughened surface.

20. The method of claim 19, wherein the step of removing an upper portion of the roughened surface includes removing the upper portion of the roughened surface such that a top edge of the roughened surface generally matches a contour the crest of the patient's jawbone.

21. The method of claim 19, wherein the step of installing the dental implant into the patient's jawbone such that the body portion lies substantially beneath a crest of a patient's jawbone and the roughened portion of the collar portion extends above the crest of a patient's jawbone further includes the step of extending the roughened portion at least approximately 2 millimeters above the crest of the patient's jawbone.

22. The method of claim 19, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 3 millimeters above the crest of the patient's jawbone.

23. The method of claim 19, wherein the step of installing the dental implant into the patient's jawbone such that the body portion lies substantially beneath a crest of a patient's jawbone and the roughened portion of the collar portion extends above the crest of a patient's jawbone further include the step of extending the roughened portion at least approximately 4 millimeters above the crest of the patient's jawbone.

* * * * *